(12) United States Patent
Gruning et al.

(10) Patent No.: US 6,288,129 B1
(45) Date of Patent: Sep. 11, 2001

(54) PROCESS FOR PREPARING ACRYLIC ESTERS AND/OR METHACRYLIC ESTERS OF HYDROXY-FUNCTIONAL SILOXANES AND/OR POLYOXYALKYLENE-MODIFIED SILOXANES AND THEIR USE

(75) Inventors: Burghard Gruning; Geoffrey Hills, both of Essen; Wolfgang Josten, Konigswinter; Dietmar Schaefer, Hattingen; Stefan Silber, Krefeld; Christian Weitemeyer, Essen, all of (DE)

(73) Assignee: Th. Goldschmidt AG, Essen (DE)

( * ) Notice: Subject to any disclaimer, the term of this patent is extended or adjusted under 35 U.S.C. 154(b) by 0 days.

(21) Appl. No.: 09/431,438

(22) Filed: Nov. 1, 1999

(30) Foreign Application Priority Data

Nov. 3, 1998 (DE) .............................................. 198 50 507

(51) Int. Cl.[7] ..................................................... B01F 17/00
(52) U.S. Cl. .............................. 516/23; 435/135; 528/26
(58) Field of Search ............................ 528/26; 435/135; 522/99; 516/23

(56) References Cited

U.S. PATENT DOCUMENTS

| | | |
|---|---|---|
| 4,130,708 | 12/1978 | Friedlander et al. . |
| 4,218,294 | 8/1980 | Brack . |
| 4,369,300 | 1/1983 | Carter et al. . |
| 4,687,811 | * 8/1987 | Sasaki et al. . |
| 4,777,265 | 10/1988 | Merger et al. . |
| 5,091,440 | 2/1992 | Griswold . |

FOREIGN PATENT DOCUMENTS

| | | |
|---|---|---|
| 27 47 233 C3 | 7/1978 | (DE) . |
| 30 44 301 A1 | 9/1981 | (DE) . |
| 39 32 460 A1 | 4/1990 | (DE) . |
| 0 518 020 A2 | 12/1992 | (EP) . |
| WO 86/02652 | 5/1986 | (WO) . |

OTHER PUBLICATIONS

R. Tor, et al., "Enzymatically Catalysed Transesterifications of Acryl and Methacryl Monomeric Esters," Enzyme Microb. Technol., vol. 12, pp. 299–304 (1990).

W. Shi, et al., "Photopolymerization of Dendritic Methacrylated Polyesters. I. Synthesis and Properties," Journal of Applied Polymer Science, vol. 59, pp. 1937–1944 (1996).

* cited by examiner

Primary Examiner—Robert Dawson
Assistant Examiner—Marc S. Zimmer
(74) Attorney, Agent, or Firm—Scully, Scott, Murphy & Presser

(57) ABSTRACT

The present invention provides a process for esterifying or transesterifying acrylic acid and/or methacrylic acid or acrylic esters and/or methacrylic esters with hydroxy-functional and/or polyoxyalkylene-modified siloxane derivatives of the general formula (I)

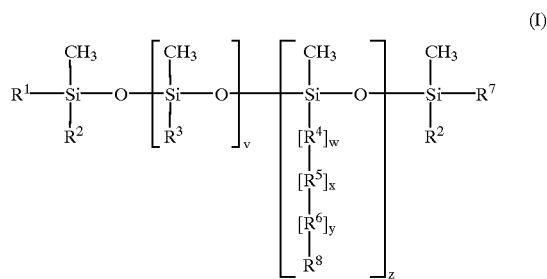

wherein $R^1$ through $R^8$ and v, w, x, y, and z are as defined herein and the esterification or transesterification reaction is catalyzed by an enzyme.

10 Claims, No Drawings

PROCESS FOR PREPARING ACRYLIC ESTERS AND/OR METHACRYLIC ESTERS OF HYDROXY-FUNCTIONAL SILOXANES AND/OR POLYOXYALKYLENE-MODIFIED SILOXANES AND THEIR USE

FIELD OF THE INVENTION

The present invention relates to a process for esterifying or transesterifying acrylic acid and/or methacrylic acid or acrylic esters and/or methacrylic esters with hydroxy-functional and/or polyoxyalkylene-modified siloxane derivatives in the presence of an enzyme which catalyzes the esterification or transesterification reaction, and to the use thereof.

BACKGROUND OF THE INVENTION

Among raw materials for the preparation of polymer products, the processing of acrylic monomers has undergone rapid development in recent years. Acrylic monomers are used predominantly in the production of fibers, dispersions, raw materials for coatings, raw materials for adhesives, and thermoplastic compositions. In smaller amounts, they serve as starting materials for a variety of chemical syntheses.

Accordingly, there are a large number of processes for preparing such acrylates and/or methacrylates. For the purposes of this invention, "acryloyl" or "methacryloyl" means a radical of the general formula

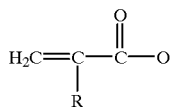

where $R=CH_3$ or H.

In addition to conventional processes for the preparation of acrylates and/or methacrylates, which correspond essentially to literature preparation processes for carboxylic esters (Review in J. March, Advanced Organic Chemistry, Wiley, 1992), there are also specifically described processes which are known in connection with the modification of hydroxy-functional siloxanes and/or polyoxyalkylene-modified siloxanes with acrylic and/or methacrylic esters or acrylic and/or methacrylic acid.

In this case, the common processes start from hydroxy-functional precursors and introduce the acryloyl and/or methacryloyl group by esterification or transesterification processes, starting from the corresponding acrylic and/or methacrylic acids or acrylic and/or methacrylic esters. In general, the presence of catalysts is unavoidable for these reactions. U.S. Pat. No. 4,777,265, for example, describes chelate complexes of titanium, zirconium, iron and zinc with 1,3-dicarbonyl compounds as catalysts for such reactions. In many cases, acids are also used to catalyze the esterification reaction, as is the case, for example, in U.S. Pat. No. 5,091,440.

These processes generally take place at temperatures above 80° C., frequently above 100° C., and require additional stabilization of the reaction mixture by means of free-radical scavenging (for example, methylhydroquinone), in order to reliably suppress unwanted polymerization of the acrylates and/or methacrylates at these temperatures. For many fields of application, the catalyst must subsequently be removed, or at least neutralized in order to avoid unwanted side reactions. This requires a complex workup procedure, in which metal oxides, metal hydroxides or corresponding salts of the metals and/or of the acids used as catalysts are formed and then, in general, removed by filtration. Such filtrations of acryloyl- and/or methacryloyl-containing reaction mixtures are complex from a technological and industrial safety standpoint and, consequently, are often lengthy. Because of the high reaction temperature, acryloyl- and/or methacryloyl-functional compounds prepared in this way frequently have an intense coloration (yellow to brownish black). This often prevents the direct use of such acryloyl and/or methacryloyl compounds in applications wherein the coloration requirements of the raw materials are stringent. In this respect mention may be made, for example, of their use as an additive in radiation-curing coatings, especially clearcoats.

Furthermore the direct reaction of alkoxy-, hydroxy- or chlorosiloxanes with hydroxy-functional acrylates and/or methacrylates is described in DE-A-27 47 233. Here again, metal catalysts, elevated temperatures above 120° C., and additional inhibitors are required. Consequently, this process is also hampered by the abovementioned disadvantages in respect of high color numbers, catalyst residues and unwanted polymerization of the acrylate and/or methacrylate groups.

In addition, there are also processes which make use of an at least difunctional linking unit by means in which (See, for example, U.S. Pat. No. 4,218,294, U.S. Pat. No. 4,369,300, U.S. Pat. No. 4,130,708, U.S. Pat. No. 4,369,300, EP-A-0 518 020, WO 86/02652 or DE-A-30 44 301) a hydroxy-functional compound is linked with a hydroxy-functional acrylate (for example, hydroxyethyl acrylate) by reaction with a diisocyanate (for example, isophorone diisocyanate) to form at least two urethane bridges with one another.

Similarly, there are also monomers available commercially which also carry an isocyanate group in the molecule (for example TMI®, meta-isoprenyl-α,α-dimethylbenzyl isocyanate; Cyanamid) and are therefore capable of reaction with alcohols. Starting from these toxicologically objectionable parent structures, a urethane group is formed which links the two structural elements to one another. The reaction between isocyanate group and hydroxyl group is generally catalyzed by the addition of catalysts (for example tin compounds or amines). These catalysts remain in the end product. Further linking reactions, by way of oxirane derivatives, for example, are described in DE-A-39 32 460, and J. Appl. Polym. Sci., Vol. 59, 1937–1944.

These processes which introduce additional functional groups into the resultant acryloyl and/or methacryloyl compounds (for example, urethanes, ureas, β-hydroxy esters, esters, etc.) have the practical disadvantage that these additional structural elements exert a limiting effect on possible further modifications to these compounds by means, for example, of secondary reactions. There may also be an undesirable effect on processing parameters, such as the viscosity. In some cases, the structure as well of the organomodified siloxane methacrylates and/or siloxane acrylates prepared in this way is influenced such that desired or unwanted surface-active properties are altered, so as to place an additional barrier in the way of systematic development work.

R. Tor, Enzyme Micro. Technol., 1990, Vol. 12, April, pp. 299–304, describes the enzymatically catalyzed transesterification of acrylic and methacrylic monomer esters for the preparation of hydroxy- and dihydroxyalkyl acrylates and methacrylates without the formation of di- or triacrylates and -methacrylates. 2-hydroxyethyl, 2-hydroxypropyl and 1,2-dihydroxypropyl esters of acrylic acid and methacrylic acid are investigated in the R. Tor disclosure.

SUMMARY OF THE INVENTION

One object of the present invention is to provide a simplified process for esterifying or transesterifying acrylic and/or methacrylic acid or acrylic and/or methacrylic esters with hydroxy-functional siloxanes and/or polyoxyalkylene-modified siloxanes. Such a preparation process should, in particular, permit a much paler color of the reaction products; should avoid the formation of byproducts (owing to nonselective catalysis); should permit simple removal of the enzyme catalyst from the product; and should avoid unwanted and uncontrolled free-radical polymerizations of the acrylate and/or methacrylate derivatives.

The abovementioned object is achieved by a process for esterifying or transesterifying acrylic acid and/or methacrylic acid or acrylic esters and/or methacrylic esters with hydroxy-functional and/or polyoxyalkylene-modified siloxane derivatives of the general formula (I)

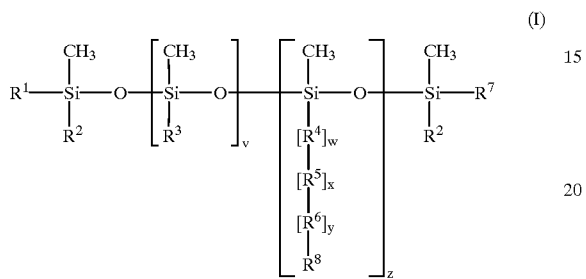

(I)

where
$R^1$ and/or $R^7=R^2$ or $[R^4]_w$—$[R^5]_x$—$[R^6]_y$—$R^8$;
$R^2$ is $R^3$ or $R^2$ is not equal to $R^3$ for identical or different alkyl radicals or alkylene radicals having 1 to 24 carbon atoms or unsubstituted or substituted phenyl radicals having up to 24 carbon atoms;
$R^4$ is a divalent radical of the formula O, NH, $NR^2$, S or a radical of the formula $(OSi(CH_3)_2)_u$, where
  u is 1 to 200;
each $R^5$ is the same or different alkyl radicals or alkylene radicals having 1 to 24 carbon atoms, or $C_nH_{2n-f}R^2_f$—$R^4$—$C_mH_{2m-g}R^2_g$, where
  f is 0 to 12;
  g is 0 to 12;
  n is 1 to 18;
  m is 1 to 18;
$R^6$ is O—$(C_2H_{4-a}R^2_aO)_b(C_cH_{2c}O)_d$, where
  a is 0 to 3;
  b is 0 to 100;
  c is 2 to 12;
  d is 0 to 100;
  the sum (b+d)=1 to 200
  and the sequence of the individual polyoxyalkylene segments $(C_2H_{4-a}R^2_aO)_b$ and $(C_cH_{2c}O)_d$ is arbitrary and, in particular, embraces block copolymers, such as random polymers and combinations thereof, or
$R^6$ is $O_e$—$C_hH_{2h}$—$C_iH_{2i-j}R^9_j$, where
  e is 0 or 1;
  h is 0 to 24;
  i is 0 to 24;
  j is 1 to 3;
  the sum (w+e)=0 to 1
and $R^9$ is in each case a divalent radical of the formula O, a hydroxyl group, a radical of the formula $C_hH_{2h}$ or a radical of the formula $C_kH_{2k-1}(OH)_1$ where
  k is 0 to 24 and
  l is 1 to 3,
$R^8$ is a hydrogen or a monovalent organic radical, if y is 1, at least one hydrogen is present per molecule, or an OH group or a monovalent organic radical if y=0, at least one OH group is present per molecule;
v is 0 to 200;
w is 0 or 1;
x is 0 or 1;
y is 0 or 1;
z is 0 to 200;
and the sum (w+x+y)=1 to 3
and if, z=0, $R^1$ and/or $R^7$ are/is $[R^4]_w$—$[R^5]_x$—$[R^6]_y$—$R^8$
and, if x=0, then w=0 as well, in the presence of an enzyme which catalyzes the esterification or transesterification.

DETAILED DESCRIPTION OF THE INVENTION

The skilled worker is aware that the above compounds are in the form of a mixture having a distribution governed essentially by the laws of statistics. The values for the indices b, d, u, v and z therefore represent average values.

Examples of siloxane derivatives which can be reacted in accordance with the present invention by enzymatically catalyzed esterification or transesterification of acrylic and/or methacrylic acid or acrylic and/or methacrylic esters are:

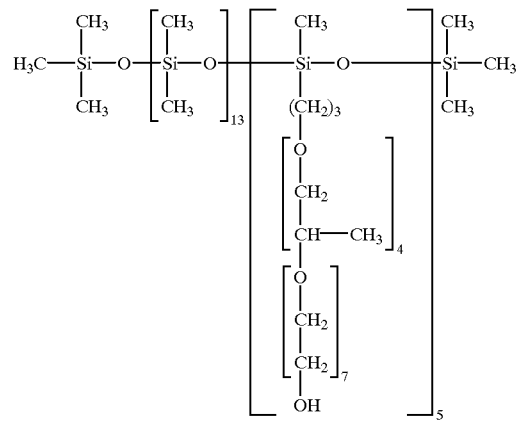

-continued
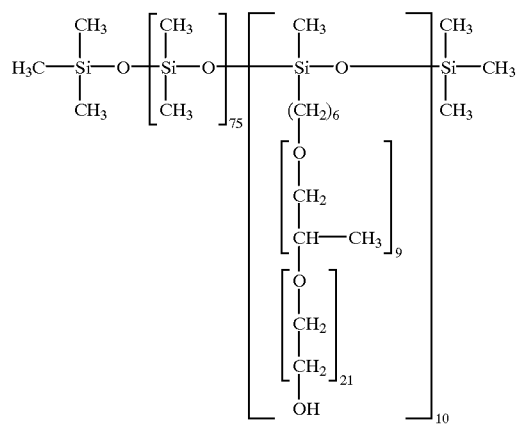
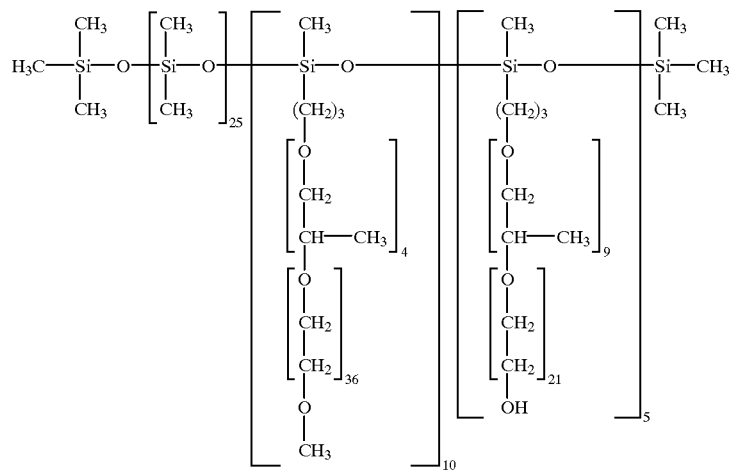
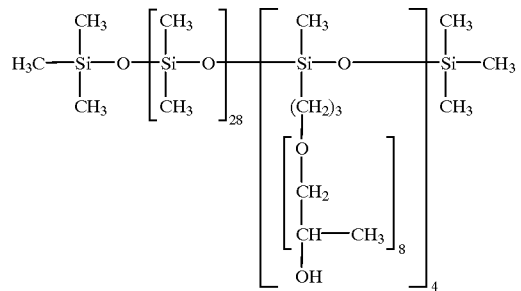
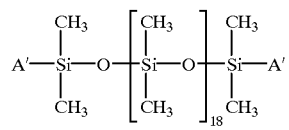
A' = (CH$_2$)$_3$—(OCH$_2$CH$_2$)$_{12}$—(OCH$_2$CH$_2$CH$_3$)$_6$—OH
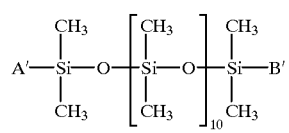
A' = (CH$_2$)$_3$—(OCH$_2$CH$_2$)$_{12}$—(OCH$_2$CHCH$_3$)$_6$—OH
B' = (CH$_2$)$_3$—(OCH$_2$CH$_2$)$_6$—(OCH$_2$CHCH$_3$)$_{14}$—OCH$_3$

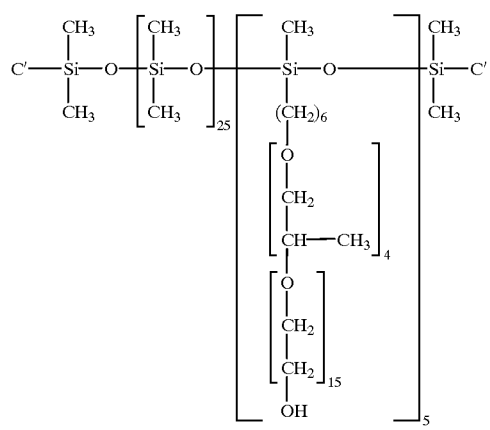
C' = (CH$_2$)$_3$—(OCH$_2$CHCH$_3$)$_4$—(OCH$_2$CH$_2$)$_{15}$—OH
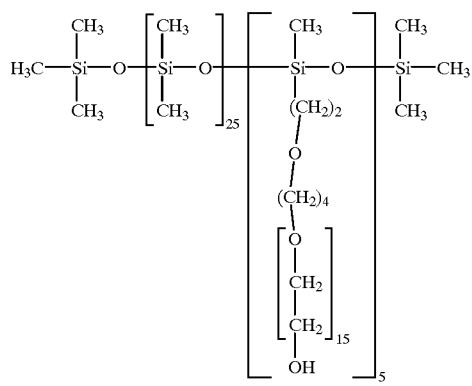
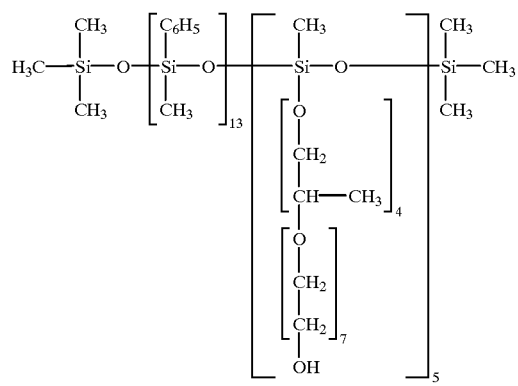
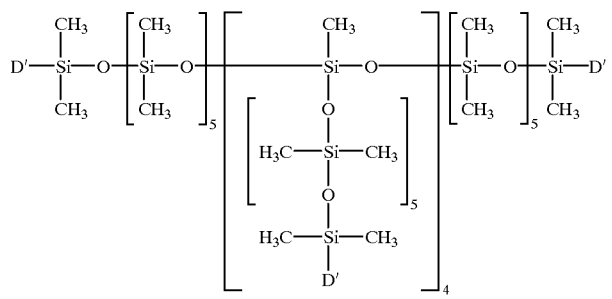
D' = (OCH$_2$CHCH$_3$)$_6$—(OCH$_2$CH$_2$)$_{20}$—OH -continued

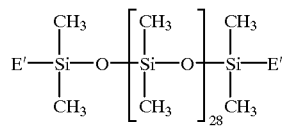

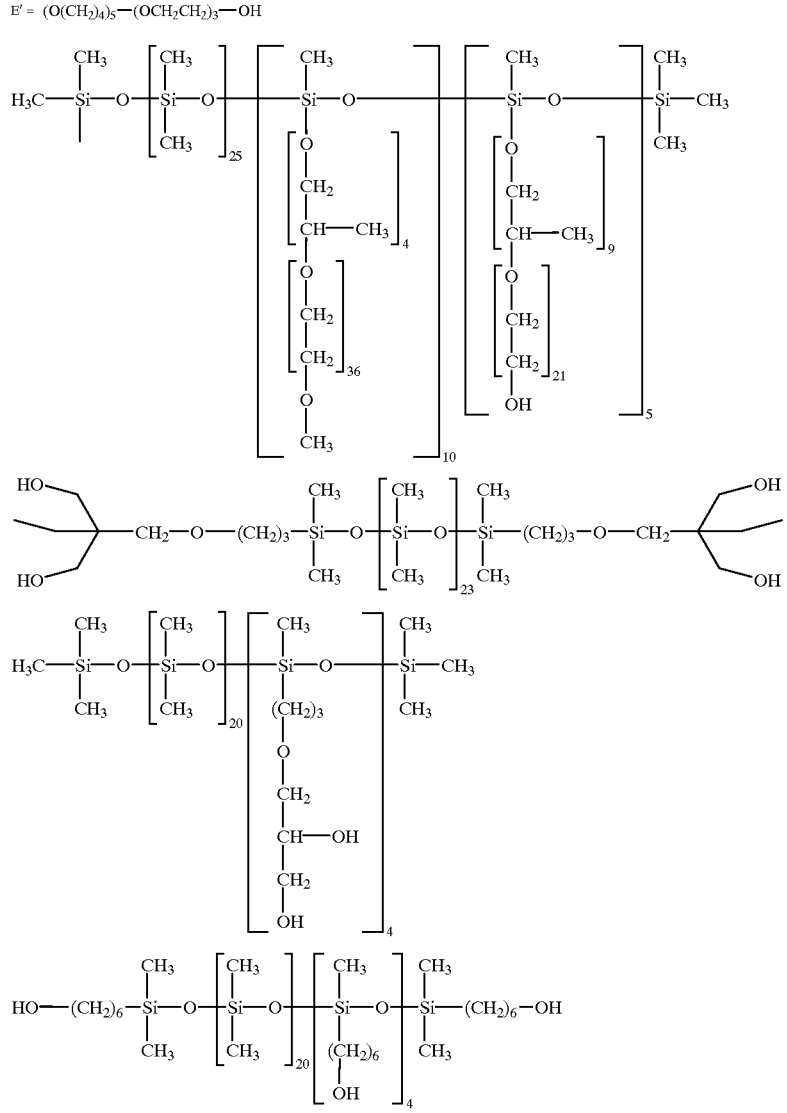

The enzymatic esterification or transesterification of acrylic and/or methacrylic acid or acrylic and/or methacrylic esters with the abovementioned compounds is carried out at low temperatures, especially from 20 to 100° C., preferably from 40 to 70° C., and under mild conditions. Such conditions are advantageous because of the relatively pale color of the product; the avoidance of the formation of byproducts which may otherwise originate, for example, from chemical catalysts; the simple removal of the enzyme catalyst from the product; and the avoidance of unwanted and uncontrolled free-radical polymerization of the acryloyl and/or methacryloyl compounds.

The acryloyl- and/or methacryloyl-functional siloxane derivatives obtainable in accordance with the present invention are notable because from 5 to 100% of all hydroxyl groups originally present have been reacted to form an acrylic and/or methacrylic ester.

The acrylation and/or methacrylation proceeds the best, in high yields, with esters of acrylic and/or methacrylic acids as donor molecules, especially methyl, ethyl or butyl methacrylate and/or acrylate.

Enzymes which can be employed in the present invention as catalysts are hydrolases, especially esterases, lipases and proteases. The enzymes can be employed in pure form or in immobilized form on a support on which they are bound chemically or physically. The amount of the enzyme catalyst, based on the modified siloxane employed, is from 0.1 to 20% by weight, preferably from 1 to 10% by weight. The reaction time depends on the amount used and on the activity of the enzyme catalyst, and is, for example, up to 48 hours, preferably up to 24 hours.

In order to arrive rapidly at high degrees of conversion under simple reaction conditions, it is advantageous to use an excess of at least 10% by weight of acrylic acid and/or methacrylic acid and/or their appropriate esters (as donors) in the reaction mixture.

The production system can be characterized either by a stirred tank reactor or by a fixed bed reactor. The stirred tank reactor can be equipped with a means of distillative removal of the alkanol liberated from the acrylic and/or methacrylic acid donor, and/or of the water liberated from the acrylic acid and/or methacrylic acid.

The reaction is carried out until the desired conversion is achieved. A reaction regime with simultaneous distillation is preferred since the removal of the water of reaction and/or alkanol of reaction leads to higher conversions in shorter reaction times, owing to the shifting of the reaction equilibrium.

In order to maximize the degree of conversion, it is necessary to remove the water and/or alkanol of reaction.

After the end of reaction, the enzyme catalyst can be separated off by means of appropriate measures, such as filtration or decantation, and can, if desired, be used any number of times.

The fixed bed reactor is charged with immobilized enzymes; the reaction mixture being pumped through a column which is packed with catalyst. By using an enzyme immobilized on a support, it is also possible to carry out the reaction in a fluidized bed reactor.

The reaction mixture can be pumped continuously through the column, the residence time and thus the desired conversion being controllable by means of the flow rate. It is also possible to pump the reaction mixture through the column in a circuit, in which case it is also possible to remove the water and/or alkanol of reaction by vacuum distillation at the same time.

Other methods of removing the water and/or alkanol of reaction can also be used, an example being absorption or pervaporation.

The following examples are given to illustrate the present invention and to demonstrate some advantages that can arise from utilizing the same.

EXAMPLE 1

408 g of a polyoxyalkylene-modified siloxane of the formula HO—[(CH(CH$_3$)CH$_2$O)(C$_2$H$_4$O)$_{3,8}$]$_4$—(C$_3$H$_6$)—Si(CH$_3$)$_2$O—(Si(CH$_3$)$_2$O)$_{18}$—Si(CH$_3$)$_2$—(C$_3$H$_6$)—[(OC$_2$H$_4$)$_{3,8}$(OCH$_2$CH(CH$_3$))]$_4$—OH were mixed with 123 g of butyl acrylate and 10.8 g of the enzyme Novozym® 435 and the mixture was heated to 70° C. The butanol liberated was distilled off under vacuum (20–40 mbar). After a reaction time of 8 h, the catalyst was filtered off and the remaining butyl acrylate was distilled off at 100–110° C. 65% of the hydroxyl groups were acrylated (determined by means of the hydroxyl number).

In terms of its performance properties as an additive for radiation-curing coatings, the product prepared in this way possessed in total properties at least equal to those of a conventionally prepared product, but have the advantage of a much lower degree of inherent coloration.

EXAMPLE 2

120 g of polyoxyalkylene-modified siloxane as in Example 1 were mixed with 180 g of butyl acrylate and the mixture was heated to 70° C. and pumped at a flow rate of 0.64 g/min through a column packed with 2 g of Novozym® 435. After 4 h, the butanol formed and the excess butyl acrylate were removed by distillation from the collected product. The result was a product having a degree of acrylation of 57% (determined by means of the hydroxyl number).

While this invention has been particularly shown and described with respect to preferred embodiments thereof, it will be understood by those skilled in the art that the foregoing and other changes in form and detail may be made without departing from the spirit and scope of the present invention. It is therefore intended that the present invention not be limited to the exact forms described and illustrated, but fall within the scope of the appended claims.

What is claimed is:

1. A method for the stabilization of a dispersion comprising adding a stabilizing effective amount of at least one modified siloxane compound to a dispersion, wherein said at least one modified siloxane compound is obtained by reacting at least one compound selected from the group consisting of acrylic acid, methacrylic acid, acrylic esters and methacrylic esters with a hydroxy-functional siloxane derivative, a polyoxyalkylene-modified siloxane derivative, or both, said siloxane derivatives having the general formula (I)

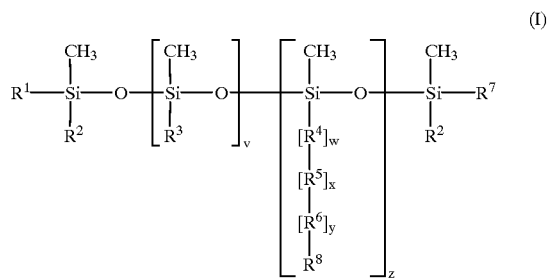

u=1 to 200;

each $R^5$ is the same or different alkyl radicals or alkylene radicals having 1 to 24 carbon atoms, or $C_nH_{2n-f}R^2{}_f$—$R^4$—$C_mH_{2m-g}R^2{}_g$, where f is 0 to 12;

g is 0 to 12;

n is 1 to 18;

m is 1 to 18;

$R^6$ is O—$(C_2H_{4-a}R^2{}_aO)_b(C_cH_{2c}O)_d$, where a is 0 to 3;

b is 0 to 100;

c is 2 to 12;

d is 0 to 100;

the sum (b+d)=1 to 200 and the sequence of the individual polyoxyalkylene segments $(C_2H_{4-a}R^2{}_aO)_b$ and $(C_cH_{2c}O)_d$ includes block copolymers, or $R^6$ is $O_e$—$C_hH_{2h}$—$C_iH_{2i-j}R^9{}_j$, where e is 0 or 1;

h is 0 to 24;

i is 0 to 24;

j is 1 to 3;

the sum (w+c)=0 to 1 and $R^9$ is in each case a divalent radical of the formula O, a hydroxyl group, a radical of the formula $C_hH_{2h}$ or a radical of the formula $C_kH_{2k-1}(OH)_l$ where k is 0 to 24 and l is 1 to 3;

$R^8$ is a hydrogen or a monovalent organic radical, if y is 1, at least one hydrogen is present per molecule, or an OH group or a monovalent organic radical, if y=0, at least one OH group is present per molecule, v is 0 to 200;

w is 0 or 1;

x is 0 or 1;

y is 0 or 1;

z is 0 to 200;

and the sum (w+x+y)=1 to 3 and if, z=0, $R^1$ and/or $R^7$ are/is $[R^4]_w-[R^5]_x-[R^6]_y-R^8$ and if, x=0, then w=0, in the presence of an enzyme which catalyzes the reaction.

2. The method of claim 1 wherein the enzyme is a hydrolase.

3. The method of claim 2 wherein the hydrolase is selected from the group consisting of a lipase, an esterase and a protease.

4. The method of claim 1 wherein said enzyme is immobilized on a support.

5. The method of claim 1 wherein the reaction is carried out at a temperature in the range from 20° to 100° C.

6. The method of claim 5 wherein the reaction temperature is from 40° to 70° C.

7. The method of claim 1 wherein methyl, ethyl, propyl or butyl esters of acrylic or methacrylic acid are employed as an acid donor.

8. The method of claim 1 wherein from 5 to 100% of the hydroxyl groups are acrylated or methacrylated.

9. The method of claim 1 wherein the enzyme is employed in an amount of from 0.1 to 20% by weight, based on the siloxane derivative.

10. The method of claim 9 wherein from 1 to 10% by weight of enzyme is employed in said reaction.

* * * * *